United States Patent [19]

Scherberich

[11] 4,245,117
[45] Jan. 13, 1981

[54] PROCESS FOR THE RECOVERY OF PURE L-CYSTINE

[75] Inventor: Paul Scherberich, Dietzenbach, Fed. Rep. of Germany

[73] Assignee: Deutsche Gold- und Silber-Scheideanstalt vormals Roessler, Frankfurt, Fed. Rep. of Germany

[21] Appl. No.: 52,240

[22] Filed: Jun. 26, 1979

Related U.S. Application Data

[62] Division of Ser. No. 849,610, Nov. 8, 1977, abandoned.

[30] Foreign Application Priority Data

Nov. 24, 1976 [DE] Fed. Rep. of Germany ....... 2653332

[51] Int. Cl.³ .......................................... C07C 149/247
[52] U.S. Cl. .................................................. 562/554
[58] Field of Search ............................... 562/554, 557

[56] References Cited

U.S. PATENT DOCUMENTS

| | | | |
|---|---|---|---|
| 2,414,303 | 1/1947 | Holloway | 260/534 S |
| 2,471,053 | 5/1949 | Almquist | 260/534 S |
| 2,650,242 | 8/1953 | Cardinal | 260/534 S |
| 2,681,927 | 6/1954 | McCollum | 260/534 S |

FOREIGN PATENT DOCUMENTS

| | | | |
|---|---|---|---|
| 645181 | 7/1962 | Canada | 260/534 S |
| 50-95221 | 7/1975 | Japan | 260/534 S |
| 695378 | 8/1953 | United Kingdom | 260/534 S |

OTHER PUBLICATIONS

Plimmer, Biochem. J., vol. 7, pp. 311–317, (1913).
Groggins, "Unit Processes in Organic Synthesis", 5th Ed., pp. 694–702, (1958).
Marvel, "Organic Syntheses", vol. 5. pp. 39 & 40, (1925).

*Primary Examiner*—Natalie Trousof
*Assistant Examiner*—Michael Shippen
*Attorney, Agent, or Firm*—Cushman, Darby & Cushman

[57] ABSTRACT

Pure L-cystine is recovered from a mixture with other aminoacids by fractional crystallization in presence of acids and water from an alcoholic medium.

22 Claims, No Drawings

PROCESS FOR THE RECOVERY OF PURE L-CYSTINE

This is a division of application Ser. No. 849,610 filed Nov. 8, 1977, now abandoned.

BACKGROUND OF THE INVENTION

The invention is directed to a process for the recovery of pure L-cystine from a mixture with other aminoacids by fractional crystallization in the presence of acids and water.

It is known to separate cystine from a mixture of aminoacids by fractional crystallization. To separate the cystine, especially from tyrosine, the crystallization takes place from dilute aqueous hydrochloric acid with addition of sodium acetate (Org. Syntheses 5 (1925) 39–41). Cystine also is separated from tyrosine and leucine by crystallization from concentrated aqueous hydrochloric acid and from glutamic acid in neutral aqueous medium (German Pat. No. 907,175). The disadvantage of these processes is that a pure cystine free from tyrosine can be produced only with considerable expense or with moderate yields.

SUMMARY OF THE INVENTION

There has now been found a process for the recovery of pure L-cystine from mixtures with other aminoacids by fractional crystallization in the presence of acids and water characterized by the crystallization taking place in alcoholic medium.

The process is suited for the recovery of L-cystine from any mixture with other aminoacids, especially for the separation of L-cystine from L-tyrosine. The process is used with particular advantage for the recovery of L-cystine from aminoacid mixture which results from the hydrolytic splitting from keratin containing natural products such as hair, bristles and claws or hooves. Keratin hydrolysis products contain glycine, alanine, valine, leucine, β-phenylalanine, serine, threonine, tyrosine, aspartic acidm glutamic acid, lysine, arginine, histidine, methionine, proline and tryptophane in addition to cystine (Org. Syntheses 5 (1925) 39–41). The process of the present invention is suitable for separating the cystine from any of these other aminoacids or any mixture of these other aminoacids. These aminoacids are alpha-amino carboxylic acids.

According to the process of the invention the L-cystine is generally so separated from the remaining aminoacids contained in the mixture by a single crystallization that it is obtained in high yields and excellent purity. Particularly despite the slight expense there is attained a trouble free separation of the L-cystine from L-tyrosine.

According to the invention the fractional crystallization takes place in alcoholic medium. There can be used monohydric or polyhydric aliphatic, cycloaliphatic and aromatic alcohols which are liquid under the reaction conditions as for example methanol, ethanol, isopropyl alcohol, n-propyl alcohol, n-butanol, sec.butyl alcohol, tert.butyl alcohol, n-hexanol, isooctyl alcohol, ethylene glycol, propanediol-1,2, trimethylene glycol, glycerine, cyclohexanol and benzyl alcohol. Preferred are monohydric alcohols, e.g., alkanols with 1 to 8 carbon atoms, particularly methanol, ethanol, propanol-2 and n-butanol. Mixtures of alcohols can also be used.

The crystallization, moreover, takes place in the presence of an acid. There can be used both organic and inorganic acids which are present as liquids under the reaction conditions or are soluble in the alcohol and/or in water and which do not decompose the aminoacids. There can be used for example aliphatic sulfonic acids such as methanesulfonic acid, methanetrisulfonic acid, propan-2-sulfonic acid, ethanesulfonic acid or aromatic sulfonic acids such as benzene sulfonic acid and p-toluene sulfonic acid, or aliphatic or cycloaliphatic carboxylic acids such as isobutyric acid, butyric acid, n-valeric acid, isovaleric acid, trimethylacetic acid, lactic acid, oxalic acid, malonic acid, adipic acid, maleic acid, succinic acid, tartaric acid, citric acid, vinyl acetic acid and especially formic acid, acetic acid and propionic acid, or araliphatic carboxylic acids such as phenyl acetic acid, mandelic acid and cinnamic acid or aromatic carboxylic acids such as benzoic acid, phthalic acid, terephthalic acid, salicylic acid, anthranilic acid, p-chlorobenzoic acid or heterocyclic carboxylic acids such as thiophene-2-carboxylic acid, furane-2-carboxylic acid, picolinic acid and isonicotinic acid, or preferably mineral acids such as sulfuric acid, phosphoric acid, hydrobromic acid and especially hydrochloric acid. These acids of course are different from the alpha-aminoacids from which the cystine is separated. Thus the organic acids do not have an amino group on the aliphatic alpha carbon atom to the carboxylic acid group. Those mentioned above are either unsubstituted hydrocarbon or heterocyclic carboxylic acids or sulfonic acid or have a hydroxy substituent or have an amino group attached to an aromatic ring.

Conventional procedures for fractional crystallization can be used to carry out the process of the invention.

The ratio of aminoacid to alcohol can be varied widely. It is not critical and depends to a certain extent on the type of materials. It is advantageous to add so much alcohol that upon heating the mixture of aminoacids, alcohol, water and acid, in a given case to the boiling point, a substantially saturated solution of the aminoacids (particularly the cystine) results.

The portion of water in the mixture likewise depends to a certain extent on the type of materials. Generally, the mixture should contain about 1 to 50 weight percent, preferably, however, not more than about 10 weight percent of water.

The ratio of aminoacid to the necessary acid can be either stoichiometric or below or above stoichiometric. However, generally it is suitable to use at least one equivalent of acid per equivalent of amino group, preferably 1 to 4 equivalents, especially 1.2 to 1.8 equivalents of acid per equivalent amino group in the aminoacid.

The L-cystine crystallizing as salt of the acid used can be converted to free L-cystine in customary manner, for example, by treating with alkaline acting materials such as alkali hydroxides, e.g., sodium hydroxide or potassium hydroxide, or ammonia.

The process can comprise, consist essentially of the steps set forth and the materials can comprise, consist essentially of or consist of the materials set forth.

Unless otherwise indicated, all parts and percentages are by weight.

In the following examples, the rotary power of the material is always given as specific rotation $[\alpha]_D^{20}$ in degrees$\times$cm$^3$/dm$\times$g. The percent data is in weight percent.

DESCRIPTION OF THE PREFERRED EMBODIMENTS

EXAMPLE 1

100 grams of an aminoacid mixture produced from a keratin containing material which contained 85% L-cystine, 10% L-tyrosine and 5% other aminoacids were mixed with 500 ml of propanol-2 and 80 ml of concentrated aqueous hydrochloric acid (about 36.5% HCl). The mixture was held for 60 minutes at 60° to 70° C. and then cooled to 20° C. for separation of the L-cystine dihydrochloride. The L-cystine dihydrochloride was filtered off, washed with propanol-2 and dried under reduced pressure. The yield was 107 grams corresponding to 97% based on the L-cystine added with the aminoacid mixture. The salt in a 5 percent solution in 1 normal aqueous hydrochloric acid had a specific rotation of −220°. According to investigations by means of thin layer chromatography and column chromatography it was free from impurities.

100 grams of L-cystine dihydrochloride were dissolved in 500 ml of water. The solution was adjusted to pH 3 by the addition of a concentrated aqueous solution of sodium hydroxide. As a result of this, the L-cystine separated out. The yield was 74 grams, corresponding to 94% based on the L-cystine dihydrochloride added. The L-cystine in a 5 percent solution in 1 N aqueous hydrochloric acid had a specific rotation of −217°. According to thin layer chromatography and column chromatography examination it was free from impurities.

The mother liquor remaining after the separation of the L-cystine was treated with a further 100 grams of the aminoacid mixture and 80 ml of concentrated aqueous hydrochloric acid for a new charge. The procedure otherwise was as previously set forth. The yield of L-cystine dihydrochloride amounted to 105 grams, corresponding to 95% based on the L-cystine added with the aminoacid mixture. The purity of the L-cystine dihydrochloride corresponded to that in the previous charge.

EXAMPLE 2

The procedure was the same as in Example 1, but there were added 500 ml of ethanol in place of propanol-2. The yield of L-cystine was 77 grams, corresponding to 91% based on the L-cystine added. The L-cystine corresponded in purity to that produced in Example 1.

EXAMPLE 3

The procedure was the same as in Example 1, but there were added 500 ml of methanol in place of propanol-2. The yield of L-cystine amounted to 75 grams, corresponding to 88% based on the L-cystine added.

EXAMPLE 4

100 grams of an aminoacid mixture containing 80% L-cystine, 15% L-tyrosine and 5% other aminoacids were mixed with 800 ml of ethanol, 50 ml water and 40 grams of formic acid. The mixture was heated and held for 15 minutes under reflux at the boiling point. Upon cooling to 20° C. the addition compound of 1 mole portion L-cystine and 2 mole portions formic acid separated out. This was filtered off and dissolved in 100 ml of water. The solution was adjusted to a pH of 3 with a 20 percent aqueous solution of sodium hydroxide. The yield of L-cystine was 71 grams, corresponding to 89% based on the L-cystine in the aminoacid mixture added. The L-cystine corresponded in purity to that produced in Example 1.

EXAMPLE 5

The procedure was the same as in Example 1, but there were added 55 grams of acetic acid in place of formic acid. The yield of L-cystine was 72 grams, corresponding to 90% based on the L-cystine added. In purity the L-cystine corresponded to that produced in Example 1.

EXAMPLE 6

A mixture of 60 grams of L-cystine and 40 grams of L-tyrosine were mixed with 1000 ml of propanol-2 and 100 ml of concentrated aqueous hydrochloric acid (36.5%). The mixture was heated and held for 30 minutes under reflux at the boiling point. The rest of the procedure was in accordance with Example 1. The yield of L-cystine was 51 grams, corresponding to 85% based on the L-cystine added. In purity the L-cystine corresponded to that produced in Example 1.

EXAMPLE 7

100 grams of crude L-cystine containing 25% of L-tyrosine were mixed with 70 ml of concentrated aqueous hydrochloric acid and 600 ml of n-butanol. The mixture was dehydrated by distillation of an azeotropic mixture of water and n-butanol. Upon cooling to 10° C. L-cystine dihydrochloride separated out. The rest of the procedure was as in Example 1. The yield of L-cystine amounted to 66 grams, corresponding to 88% based on the L-cystine added in the crude product. The purity corresponded to that of the L-cystine produced in Example 1.

What is claimed is:

1. In a process for the recovery of pure L-cystine from a mixture with other amino carboxylic acid by fractional crystallization in the presence of an acid other than said amino carboxylic acids and water and wherein said other amino carboxylic acids include at least one selected from the group consisting of glycine, alanine, valine, leucine, β-phenylalanine, serine, threonine, tyrosine, aspartic acid, glutamic acid, lysine, argenine, histidine, methionine, proline and tryptophane, the improvement comprising starting with a mixture of said amino carboxylic acids, an alcoholic medium, water and an acid other than said amino carboxylic acids and carrying out the crystallization of the salt of L-cystine and the acid in said water containing alcoholic medium, there being present from said start 1 to 50 weight percent of water based on the total weight of the mixture of L-cystine, other amino carboxylic acid, alcoholic medium, water and acid other than an amino carboxylic acid.

2. A process according to claim 1 wherein the alcohol is methanol, ethanol, propanol-2 or n-butanol.

3. A process according to claim 1 wherein the alcohol is a water soluble alkanol having 1 to 4 carbon atoms.

4. A process according to claim 1 wherein the alcohol is a water soluble alkanol or glycol.

5. A process according to claim 1 wherein the alcohol is an alkanol of 1 to 6 carbon atoms, an alkanediol of 2 to 3 carbon atoms, cyclohexanol or benzyl alcohol.

6. A process according to claim 1 wherein over 50% of the aminoacids is L-cystine.

7. A process according to claim 6 wherein 60 to 85% of the aminoacids is L-cystine.

8. A process according to claim 1 wherein the acid employed to form the salt is a mineral acid or a water soluble alkanoic acid.

9. A process according to claim 8 wherein the acid employed to form the salt is a mineral acid.

10. A process according to claim 9 wherein the acid is hydrochloric acid.

11. A process according to claim 1 wherein the acid employed is an aliphatic sulfonic acid, an aromatic sulfonic acid, an unsubstituted aliphatic carboxylic acid, an unsubstituted aromatic carboxylic acid, an unsubstituted heterocyclic carboxylic acid, a chloro substituted aromatic carboxylic acid, a hydroxy substituted aliphatic carboxylic acid, a hydroxy substituted aromatic carboxylic acid, an unsubstituted araliphatic carboxylic acid, a hydroxy substituted araliphatic carboxylic acid or a mineral acid.

12. A process according to claim 1 wherein there is employed 1 to 4 equivalents of the acid per equivalent of amino groups in the amino carboxylic acid.

13. A process according to claim 1 wherein the mixture of aminoacids, acid and alcohol is heated and the hot mixture is cooled to form the crystallized salt of L-cystine and the acid.

14. A process according to claim 1 wherein L-cystine is separated from L-tyrosine.

15. A process according to claim 14 wherein the alcohol is methanol, ethanol, propanol-2 or n-butanol.

16. A process according to claim 14 wherein the alcohol is an alkanol of 1 to 6 carbon atoms, alkanediol of 2 to 3 carbon atoms, cyclohexanol or benzyl alcohol.

17. A process according to claim 16 wherein over 50% of the aminoacids is L-cystine.

18. A process according to claim 17 wherein 60 to 85% of the aminoacids is L-cystine.

19. A process according to claim 14 wherein the acid employed to form the salt is a mineral acid or a water soluble alkanoic acid.

20. A process according to claim 19 wherein the acid employed to form the salt is a mineral acid.

21. A process according to claim 20 wherein the acid is hydrochloric acid.

22. A process according to claim 1 wherein the mixture contains 1 to 10% water.

* * * * *